US009980776B2

(12) United States Patent
Peng et al.

(10) Patent No.: US 9,980,776 B2
(45) Date of Patent: *May 29, 2018

(54) SIDE-FIRING FIBER DELIVERY DEVICE WITH ACTIVE COOLING CAP

(71) Applicant: Boston Scientific Scimed, Inc., Maple Grove, MN (US)

(72) Inventors: Yihlih Peng, Fremont, CA (US); Gerald M. Mitchell, Los Altos, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/253,313

(22) Filed: Aug. 31, 2016

(65) Prior Publication Data

US 2016/0367320 A1 Dec. 22, 2016

Related U.S. Application Data

(63) Continuation of application No. 14/471,945, filed on Aug. 28, 2014, now Pat. No. 9,456,871, which is a (Continued)

(51) Int. Cl.
*A61B 18/24* (2006.01)
*G02B 6/26* (2006.01)
(Continued)

(52) U.S. Cl.
CPC .............. *A61B 18/24* (2013.01); *A61B 18/22* (2013.01); *G02B 6/241* (2013.01); *G02B 6/262* (2013.01);
(Continued)

(58) Field of Classification Search
CPC . A61B 18/24; A61B 2018/2272; A61B 18/18; A61B 1/015; A61B 18/22;
(Continued)

(56) References Cited

U.S. PATENT DOCUMENTS 4,325,006 A 4/1982 Norton
4,572,609 A 2/1986 Sakuragi et al.
(Continued)

FOREIGN PATENT DOCUMENTS

CN 1617039 A 5/2005
EP 0407229 A3 1/1991
(Continued)

OTHER PUBLICATIONS

Gosnell, T.R., "Laser cooling of a solid by 65 K starting from room temperature", Optics Letters, vol. 24, No. 15, Aug. 1999, pp. 1041-1043.
(Continued)

*Primary Examiner* — Scott T Luan
(74) *Attorney, Agent, or Firm* — Bookoff McAndrews, PLLC

(57) ABSTRACT

A medical laser system and related methods of utilizing cooling within and around an optical fiber tip to prevent premature failure of the optical fiber. The optical fiber is surrounded by protective jacket assembly including a body tube assembly and a tip cap assembly. The body tube assembly includes an internal fiber jacket and an external body tube with a body tube channel defined therebetween. The tip cap assembly includes an inner cap member and an outer cap member defining a cap irrigation channel therebetween. Together, the cap irrigation channel and body tube channel cooperatively define an internal irrigation channel. The optical fiber can be delivered to a treatment location through a cystoscope. Saline is directed through an external irrigation channel between the cystoscope and the protective jacket assembly as well as the internal irrigation channel to cool the fiber tip and prevent overheating and failure of the optical fiber.

20 Claims, 5 Drawing Sheets

Related U.S. Application Data continuation of application No. 12/185,592, filed on Aug. 4, 2008, now Pat. No. 8,858,542.

(60) Provisional application No. 60/953,721, filed on Aug. 3, 2007.

(51) Int. Cl.
| | | |
|---|---|---|
| *A61B 18/22* | (2006.01) | |
| *G02B 6/24* | (2006.01) | |
| *G02B 6/44* | (2006.01) | |
| *A61B 18/00* | (2006.01) | |

(52) U.S. Cl.
CPC .......... *G02B 6/443* (2013.01); *G02B 6/4415* (2013.01); *A61B 2018/00023* (2013.01); *A61B 2018/00029* (2013.01); *A61B 2018/2205* (2013.01); *A61B 2018/2244* (2013.01); *A61B 2018/2272* (2013.01)

(58) Field of Classification Search
CPC .......... A61B 2018/00029; A61B 2018/00023; A61B 2018/2205; A61B 2018/2244; G02B 6/241; G02B 6/4415; G02B 6/443; G02B 6/262

See application file for complete search history.

(56) References Cited

U.S. PATENT DOCUMENTS

| | | |
|---|---|---|
| 4,694,828 A | 9/1987 | Eichenbaum |
| 4,707,073 A | 11/1987 | Kocher |
| 4,806,289 A | 2/1989 | Laursen et al. |
| 4,832,024 A * | 5/1989 | Boussignac .......... A61B 18/245 606/15 |
| 4,945,457 A | 7/1990 | Yazdani et al. |
| 5,064,271 A | 11/1991 | Kern et al. |
| 5,076,653 A | 12/1991 | Kayashima et al. |
| 5,203,780 A | 4/1993 | Liebler |
| 5,222,174 A | 6/1993 | Miles |
| 5,320,617 A | 6/1994 | Leech |
| 5,409,483 A | 4/1995 | Campbell et al. |
| 5,416,878 A | 5/1995 | Bruce |
| 5,437,660 A | 8/1995 | Johnson et al. |
| 5,471,553 A | 11/1995 | Teshima |
| 5,496,307 A | 3/1996 | Daikuzono |
| 5,496,309 A * | 3/1996 | Saadat .................. A61B 18/24 606/15 |
| 5,571,151 A | 11/1996 | Gregory |
| 5,593,404 A | 1/1997 | Costello et al. |
| 5,737,473 A | 4/1998 | Nath |
| 5,760,364 A | 6/1998 | Marlier et al. |
| 5,762,493 A | 6/1998 | Rechmann |
| 5,785,704 A | 7/1998 | Bille et al. |
| 5,836,941 A | 11/1998 | Yoshihara et al. |
| 5,925,012 A | 7/1999 | Murphy-Chutorian et al. |
| 5,999,678 A | 12/1999 | Murphy-Chutorian et al. |
| 6,229,939 B1 | 5/2001 | Komine |
| 6,299,599 B1 | 10/2001 | Pham et al. |
| 6,343,174 B1 | 1/2002 | Neuberger |
| 6,554,824 B2 | 4/2003 | Davenport et al. |
| 6,574,401 B2 | 6/2003 | Neuberger |
| 6,802,838 B2 | 10/2004 | Loeb et al. |
| 6,888,097 B2 | 5/2005 | Batarseh |
| 6,981,804 B2 | 1/2006 | Jian |
| 6,986,764 B2 | 1/2006 | Davenport et al. |
| 7,331,954 B2 | 2/2008 | Temelkuran et al. |
| 7,457,502 B2 | 11/2008 | Davis |
| 7,463,801 B2 | 12/2008 | Brekke et al. |
| 8,858,542 B2 | 10/2014 | Peng et al. |
| 2003/0199860 A1 | 10/2003 | Loeb et al. |
| 2006/0224148 A1 | 10/2006 | Cho et al. |
| 2007/0219544 A1 | 9/2007 | Gowda et al. |
| 2007/0270788 A1 | 11/2007 | Nahen et al. |
| 2008/0195085 A1 | 8/2008 | Loeb |

FOREIGN PATENT DOCUMENTS

| | | |
|---|---|---|
| EP | 00610991 A2 | 8/1994 |
| EP | 0561903 B1 | 7/1995 |
| EP | 01992301 A1 | 11/2008 |
| JP | 07080086 A2 | 3/1995 |
| JP | 28036025 A2 | 2/2008 |
| WO | WO 2006/107522 A2 | 10/2006 |

OTHER PUBLICATIONS

Hashimoto, D., "Cooling an optical fiber to 4.5 K by indirect thermal contact with a liquid-helium . . . " Rev. Sci. Instr. 79, 093102 (2008) 5 pgs.

Maclaurin, P. et al., "Quantitative in Situ Monitoring of an Elevated Temperature Reaction Using a Water-Cooled Mid-Infrared Fiber-Optic Probe", Anal. Chem. 1996, 68, 116-1123.

Tokita, S. et al., "Liquid-cooled 24 W mid-infrared Er:ZBLAN fiber laser", Optics Letters, vol. 34, No. 20, Oct. 2009, pp. 3062-3064.

Vaskopulous, T., et al. "Cooling of optical fiber in aiding and opposing forced gas flow".

Office Action from related U.S. Appl. No. 12/185,592, dated Jun. 6, 2012.

Final Office Action from related U.S. Appl. No. 12/185,592, dated Oct. 11, 2012.

Office Action from related U.S. Appl. No. 12/185,592, dated Nov. 20, 2013.

Final Office Action from related U.S. Appl. No. 12/185,592, dated Apr. 28, 2014.

\* cited by examiner

SIDE-FIRING FIBER DELIVERY DEVICE WITH ACTIVE COOLING CAP

PRIORITY CLAIM

This Application is a continuation of U.S. application Ser. No. 14/471,945, filed Aug. 28, 2014, which is a continuation of U.S. application Ser. No. 12/185,592, filed Aug. 4, 2008, now U.S. Pat. No. 8,858,542, which claims priority to U.S. Provisional Application No. 60/953,721, filed Aug. 3, 2007. The contents all of are incorporated herein by reference in their entireties.

FIELD OF THE INVENTION

This invention relates to the field of medical lasers utilizing optical fibers. More specifically, the present invention relates to a side-firing optical fiber utilizing internal and external cooling streams to prevent premature failure at a fiber tip.

BACKGROUND OF THE INVENTION

Medical lasers have been used in treatment procedures involving various practice areas, including, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of laser energy, and often the area to which the laser energy is to be delivered is located deep within the body; for example, at the prostate or at the fallopian tubes. Due to the location of the target tissue deep within the body, the medical procedure requires that the optical fiber be flexible and maneuverable. Various light sources can be used with optical fiber devices dependent upon the requirements for the light source; for example, pulsed lasers, diode lasers and neodymium lasers can be used as light sources. Representative lasers used in medical treatment procedures include Ho:YAG lasers and Nd:YAG lasers.

In medical procedures utilizing laser energy, the laser is coupled to an optical fiber adapted to direct laser radiation from the laser, through the fiber and to the treatment area. Typically, a surgical probe is utilized in the treatment of body tissue with laser energy. The surgical probe generally includes an optical fiber coupled to a laser source, and the probe tip is positioned on the optical fiber opposite the laser source, such that the tip of the probe can be positioned adjacent to the targeted tissue. Laser energy is directed out of the probe tip of the optical fiber onto desired portions of the targeted tissue.

Depending upon the operational conditions during laser treatment, a cap on the surgical probe can overheat. Overheating of the cap can lead to failure of the optical fiber. If the optical fiber fails, the laser system fails. Overheating of the cap can cause the cap to burn, detach, or even shatter during treatment inside the patient, which can lead to injury to the patient.

SUMMARY OF THE INVENTION

The present invention comprises a medical laser system and related methods of utilizing cooling within and around an optical fiber tip so as to prevent premature failure of the optical fiber. The optical fiber comprises an internal fiber jacket having a fiber tip for directing laser energy from the optical fiber. The optical fiber is generally surrounded by a body tube and a tip cap assembly. The tip cap assembly generally comprises an inner cap member and an outer cap member. The outer cap member includes a side port positioned within an exterior surface. An internal irrigating channel is defined between the inner cap member and the outer cap member. The optical fiber is generally configured for insertion through a cystoscope such that the fiber tip can be positioned proximate a treatment location. Once the fiber tip is properly positioned, saline can be directed through the irrigating channel as well as between the cystoscope and the exterior surface to cool the optical fiber and prevent overheating and subsequent failure of the optical fiber. In addition, the use of the outer cap member provides a barrier between the fiber tip and treatment location so as to prevent adhesion of ablated tissue to the fiber tip.

In one aspect, the present invention is directed to an optical fiber having a tip cap assembly defining an internal irrigation channel. The optical fiber can be configured for insertion into a cystoscope wherein saline can be simultaneously directed through the internal irrigation channel and between the cystoscope and an exterior surface of the tip cap assembly. By continually circulating saline both internally and externally of the fiber tip, overheating of the fiber tip is prevented so as to prevent premature failure of the optical fiber.

In another aspect, the present invention is directed to a method for preventing overheating of an optical fiber. The method comprises providing an optical fiber having an internal irrigation channel at a fiber tip. The method further comprises circulating saline through the internal irrigation channel to remove heat energy from the fiber tip. The method further comprises circulating a cooling saline between a cystoscope and an exterior surface of the fiber tip. The method can further comprise providing a physical barrier between a discharge portion of the optical fiber and the treatment location to prevent adhesion of ablated tissue to the optical fiber.

In yet another aspect, the present invention is directed to a medical laser treatment system comprising a laser unit and an optical fiber capable of being introduced to a treatment location with a cystoscope. A fiber tip of the optical fiber is capable of being cooled simultaneously with an external cooling stream between the cystoscope and protective jacket assembly as well as through an internal irrigation channel defined by a tip cap assembly.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

These as well as other objects and advantages of this invention, will be more completely understood and appreciated by referring to the following more detailed description of the presently preferred exemplary embodiments of the invention in conjunction with the accompanying drawings of which.

Figure 1:
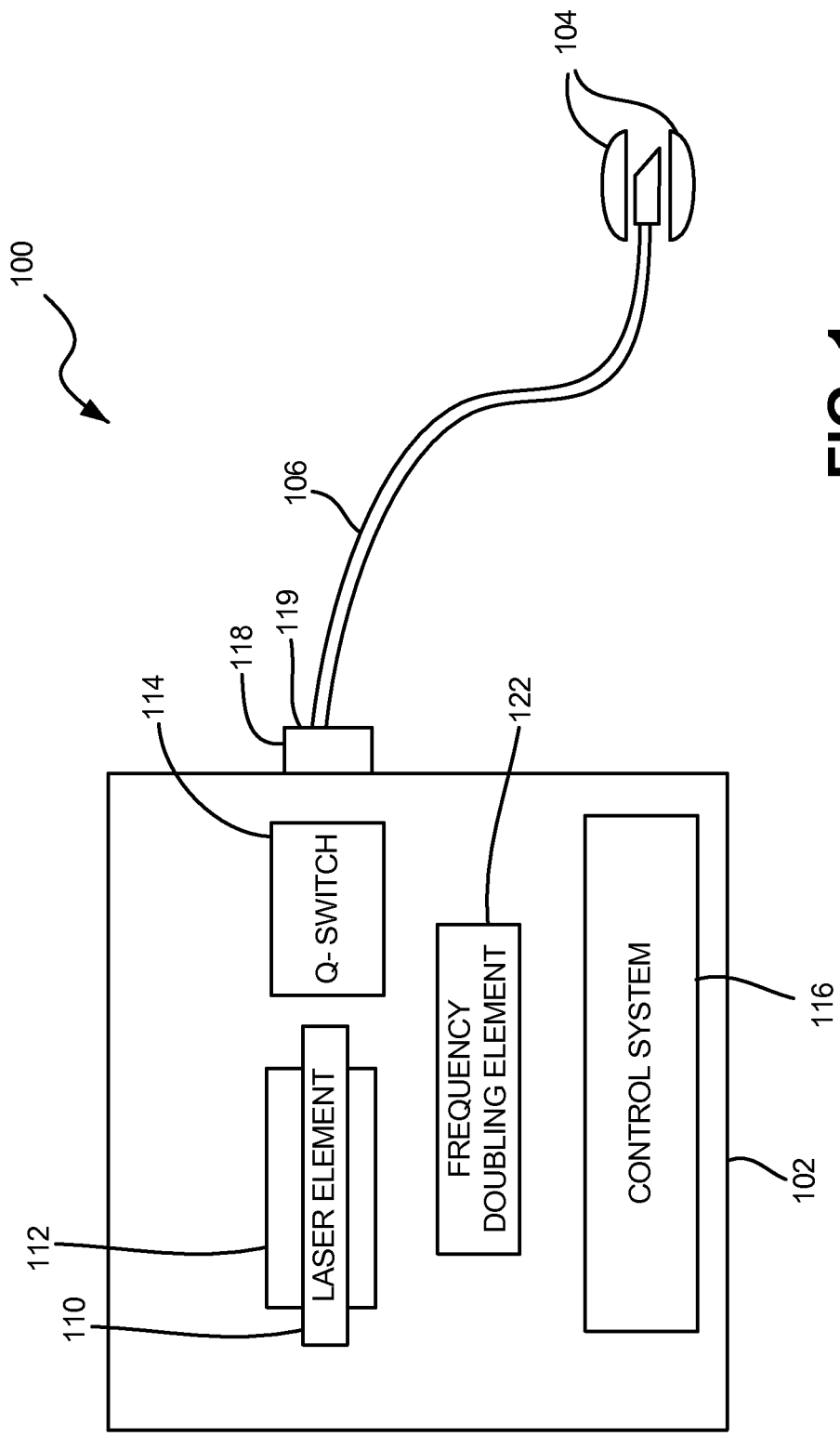
FIG. 1 is a block diagram illustration of a laser system according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF THE DRAWINGS

The present invention comprises an optical fiber for use with a medical laser system that utilizes internal and external cooling streams and related methods of monitoring an optical fibers to determine if an optical fiber cap on the optical fiber is in imminent danger of cap failure. The laser system includes a photodetector for converting returned light from the optical fiber cap to an electronic signal for comparison to a trigger threshold value known to be indicative of imminent fiber cap failure. The returned light can be the main laser treatment wavelength, an auxiliary wavelength such as an aiming beam or infrared wavelengths generated by a temperature of the optical fiber cap. In the event the electronic signal reaches the trigger threshold value, the laser system can be temporarily shut-off or the power output can be reduced. In one preferred embodiment, the present invention can be utilized as part of a Greenlight HPS system manufactured by American Medical Systems of Minnetonka, Minn. and as described in U.S. Pat. Nos. 6,554,824 and 6,986,764, which are herein incorporated by reference.

Referring to FIG. 1, there is depicted a block diagram showing an exemplary laser system 100 which may be employed for implementing the present invention. Laser system 100 includes a solid-state laser unit 102, which is used to generate laser light for delivery through optical fiber 106 to target tissue 104. Laser unit 102 is capable of being operated in a pulsed mode or continuous wave.

Laser unit 102 more specifically comprises a laser element assembly 110, pump source 112, and frequency doubling crystal 122. In the preferred-embodiment, laser element 110 outputs 1064 nm light which is focused into frequency doubling crystal 122 to create 532 nm light. According to one implementation, laser element assembly 110 may be neodymium doped YAG (Nd:YAG) crystal, which emits light having a wavelength of 1064 nm (infrared light) when excited by pump source 112. Laser element 110 may alternatively be fabricated from any suitable material wherein transition and lanthanide metal ions are disposed within a crystalline host (such as YAG, Lithium Yttrium Fluoride, Sapphire, Alexandrite, Spinel, Yttrium Orthoaluminate, Potassium Gadolinium Tungstate, Yttrium Orthovandate, or Lanthahum Scandium Borate). Laser element 110 is positioned proximal to pump source 112 and may be arranged in parallel relation therewith, although other geometries and configurations may be employed.

Pump source 112 may be any device or apparatus operable to excite laser element assembly 110. Non-limiting examples of devices which may be used as pump source 112, include: arc lamps, flashlamps, and laser diodes.

A Q-switch 114 disposed within laser unit 102 may be operated in a repetitive mode to cause a train of micropulses to be generated by laser unit 102. Typically the micropulses are less than 1 microsecond in duration separated by about 40 microseconds, creating a quasi-continuous wave train. Q-switch 114 is preferably of the acousto-optic type, but may alternatively comprise a mechanical device such as a rotating prism or aperture, an electro-optical device, or a saturable absorber.

Laser unit 102 is provided with a control system 116 for controlling and operating laser unit 102. Control system 116 will typically include a control processor which receives input from user controls (including but not limited to a beam on/off control, a beam power control, and a pulse duration control) and processes the input to accordingly generate output signals for adjusting characteristics of the output beam to match the user inputted values or conditions. With respect to pulse duration adjustment, control system 116 applies an output signal to a power supply (not shown) driving pump source 112 which modulates the energy supplied thereto, in turn controlling the pulse duration of the output beam. Laser unit 102 further includes an output port 118 couplable to a proximal end 119 of optical fiber 106. Output port 118 directs the light generated by laser unit 102 into optical fiber 106 for delivery to tissue 104.

Although FIG. 1 shows an internal frequency doubled laser, it is only by way of example. The infrared light can be internally or externally frequency doubled using non-linear crystals such as KTP, Lithium Triborate (LBO), or Beta Barium Borate (BBO) to produce 532 nm light. The frequency doubled, shorter wavelength light is better absorbed by the hemoglobin and char tissue, and promotes more efficient tissue ablation.

Figure 2:
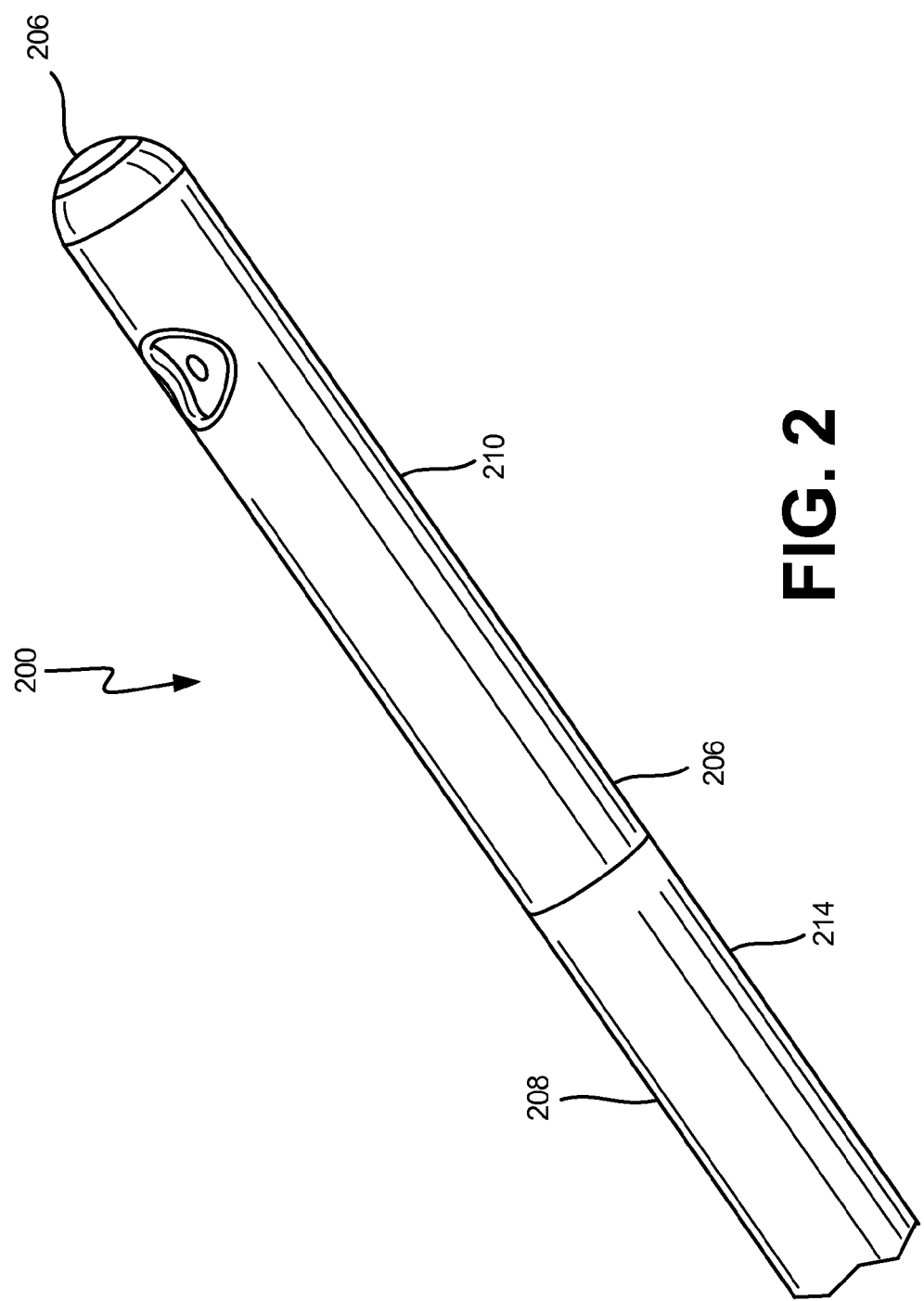
FIG. 2 is a perspective end view of an optical fiber according to an embodiment of the present invention.
Figure 3:
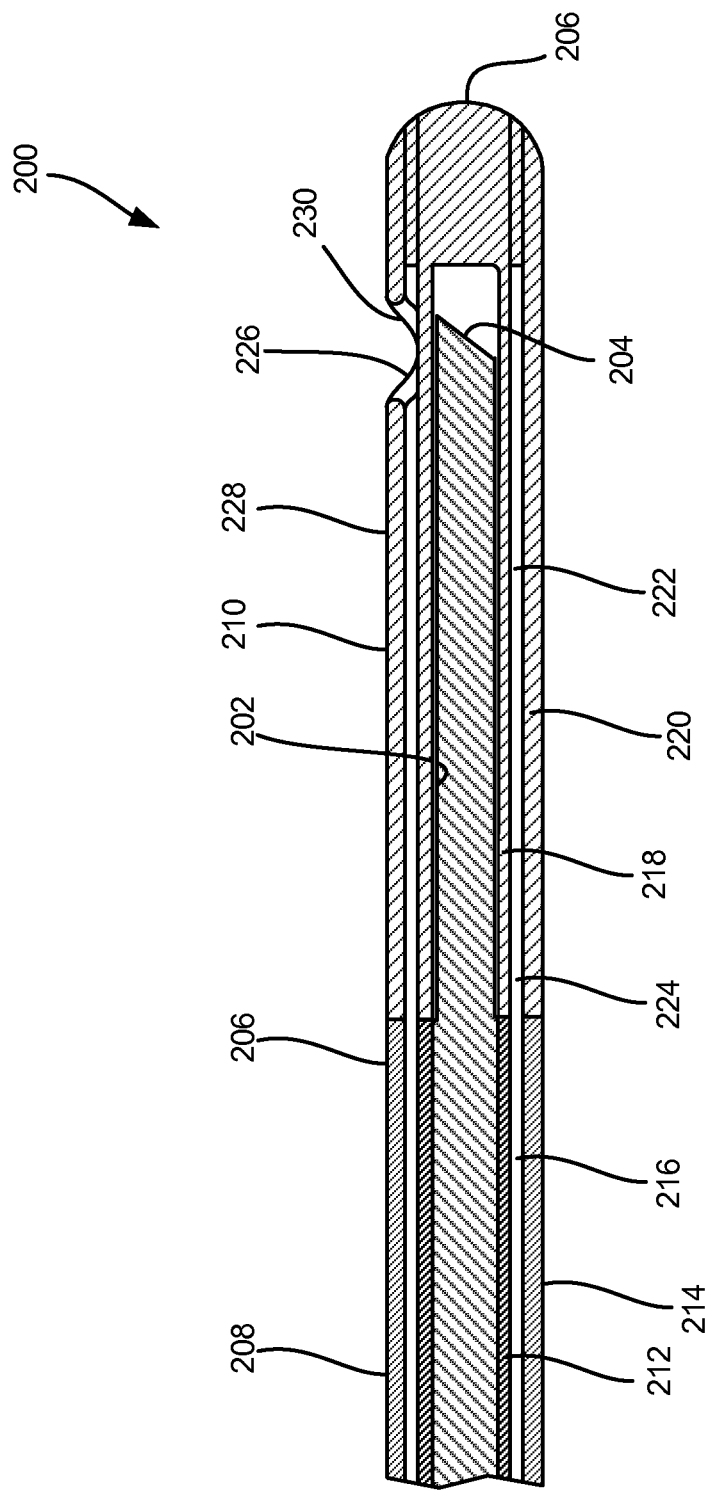
FIG. 3 is a section view of the optical fiber of FIG. 2.

Referring now to FIGS. 2 and 3, optical fiber 200 of the present invention generally comprises an internal fiber 202 defining a fiber tip 204 at a treatment end 206 of the optical fiber 200. Internal fiber 202 is manufactured from a silicon material, typical of optical fibers. Internal fiber 202 is protected from damage prior to use and during introduction to the treatment location with a protective jacket assembly 206. Projective jacket assembly 206 generally comprises a body tube assembly 208 and a tip cap assembly 210. Body tube assembly 208 generally protects a majority portion of the internal fiber 202, extending from proximal end 119 to the tip cap assembly 210. Body tube assembly 208 generally comprise an internal fiber jacket 212 and an external body tube 214 with a body tube channel 216 defined therebetween. Similar to internal fiber 202, internal fiber jacket 212 and external body tube 214 are constructed of a suitable silicon material.

As illustrated in FIG. 3, tip cap assembly 128 generally comprises an inner cap member 218 and an outer cap member 220 defining a cap irrigation channel 222 therebetween. Together, cap irrigation channel 222 and body tube channel 216 cooperatively define an internal irrigation channel 224. Outer cap member 220 includes a side port 226 positioned within an exterior surface 228. Side port 226 generally defines a radiused edge 230 such that laser energy can be directed from the fiber tip 204 to the treatment location.

Figure 4:
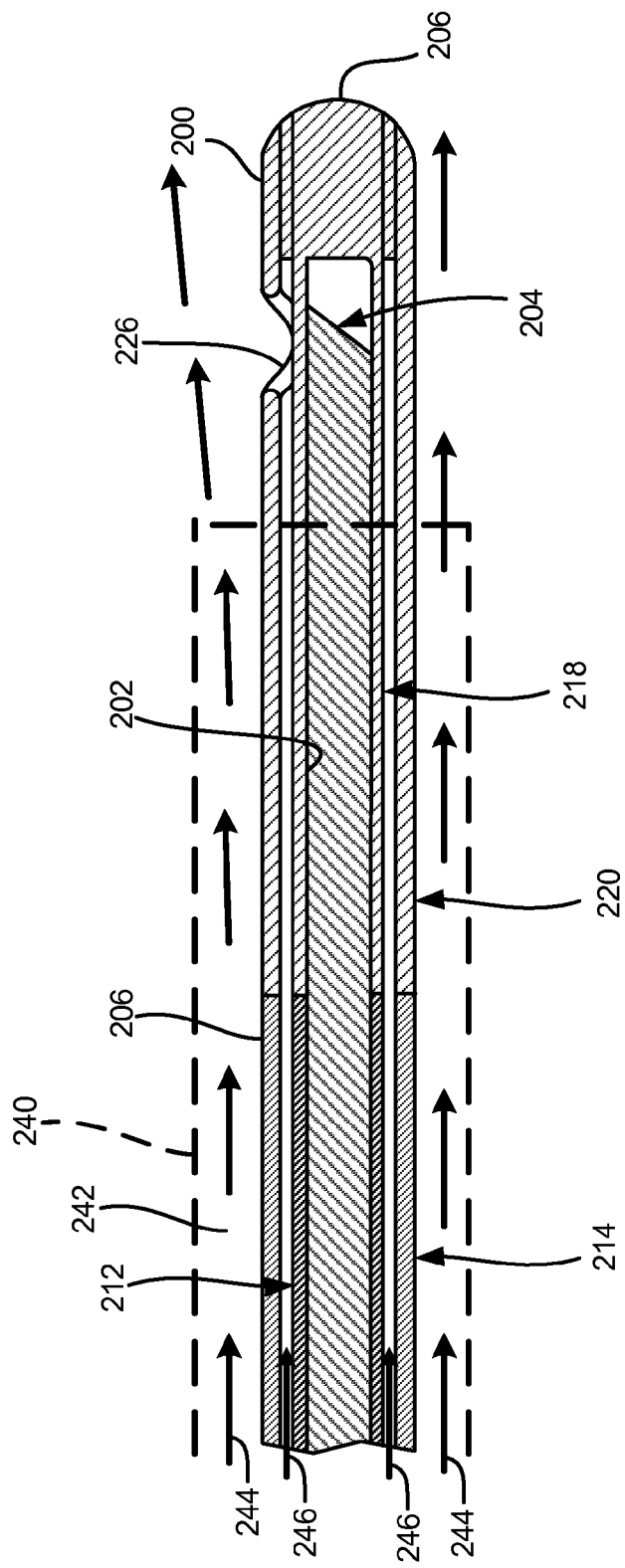
FIG. 4 is a section view of the optical fiber of FIG. 2 being introduced to a treatment location with a cystoscope according to an embodiment of the present invention.

In operation, optical fiber 200 and more specifically fiber tip 204 can be introduced to the treatment location utilizing a conventional cystoscope 240 as shown in FIG. 4. Generally, the cystoscope 240 is advanced through the urethra and proximate the treatment area. Once the cystoscope 240 is positioned at the treatment area, an irrigant such as water or saline can be injected through the cystoscope 240. When performing a medical laser procedure with the laser system 100, optical fiber 200 is advanced through the cystoscope 240 such that side port 226 is positioned proximate the desired treatment location.

With the side port 226 oriented toward the treatment location, saline is simultaneously directed through the internal irrigation channel 224 and in an external irrigation channel 242 defined between the cystoscope 240 and the protective jacket assembly 206. With an external cooling stream 244 flowing across exterior surface 228 and between the inner cap member 218 and an internal cooling stream 246 flowing between the outer cap member 220, control system 116 directs laser energy through the optical fiber 200 such that a treatment beam exits the fiber tip 204 and out the side port 226. As the treatment beam contacts the treatment location, heat is generated at a tissue surface as the laser energy ablates the targeted tissue. The dual simultaneous cooling of the external cooling stream 244 and the internal cooling stream 246 remove heat energy from the fiber tip 204. As fiber tip 204 is prevented from overheating, ablated tissue is kept from adhering within or around the side port 226 or to the exterior surface 228. In addition, the outer cap member 220 provides a gap between the fiber tip 204 and the treatment location such that tissue does not attach to the fiber tip 204 due to localized heating at the fiber tip 204. With heat energy removed at the tip cap assembly 210, overheating is avoided such that devitrification and cratering of optical fiber 200 does not occur.

Figure 5:
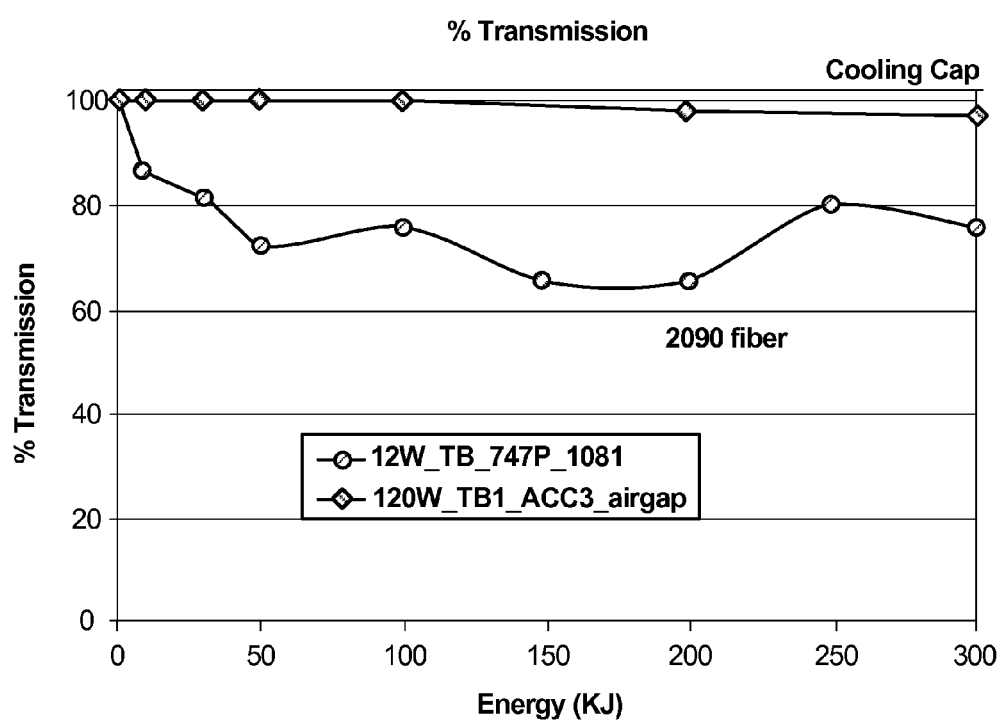
FIG. 5 is a graph comparing percentage of transmission of a optical fiber (2090 fiber) to an optical fiber with active cooling cap of the present invention.

FIG. 5 provides a comparison between the standard 2090 fiber that is typically used with a GreenLight HPS laser treatment device for treatment of benign prostate hyperplasia (BPH) and the fiber with active cooling cap of the present invention. As shown the percentage of transmission of light stays steady in the fiber with the active cooling cap while the 2090 fiber experiences intermittent decreases in transmission of light as energy is increased. As indicated by the graph, the active cooling cap fiber of the present invention provides reduced laser energy absorption by preventing the tissue contact at the laser firing point and the areas adjacent to the firing point; the tissue is in contact with the outer cap rather than the inner cap through which the laser light is being delivered. Further, the irrigation fluid from the about the inner cap pushes the tissue debris out of the firing point of the inner cap and, hence, further prevents tissue debris from depositing and burning at the firing point. Moreover, the active cooling cap of the present invention can provide cooling from inside of the cap even when the irrigation fluid from the cystoscope is totally block by tissue.

Although specific examples have been illustrated and described herein, it will be appreciated by those of ordinary skill in the art that any arrangement calculated to achieve the same purpose could be substituted for the specific examples shown. This application is intended to cove adaptations or variations of the present subject matter. Therefore, it is intended that the invention be defined by the attached claims and their legal equivalents.

We claim:

1. An optical fiber cap, comprising:
    an outer cap member including a proximal end, a distal end, an exterior surface extending therebetween, and an exit port extending through the exterior surface;
    an inner cap member including a distal end attached to the distal end of the outer cap member, an inner surface configured to receive a distal portion of an optical fiber, and a laser firing point; and
    a reflective surface configured to direct laser energy from the optical fiber, through the laser firing point, and out of the exit port in an exit direction transverse to a longitudinal axis of the optical fiber, wherein the distal end of the inner cap member and the distal end of the outer cap member are both distal to the reflective surface.

2. The optical fiber cap of claim 1, wherein the exterior surface of the outer cap member is spaced apart from the inner surface of the inner cap member in the exit direction at a location adjacent the laser firing point.

3. The optical fiber cap of claim 2, wherein a space is formed between the outer and inner cap members.

4. The optical fiber cap of claim 3, wherein the space is a fluid flow channel is configured to direct a fluid out of the exit port in the exit direction.

5. The optical fiber cap of claim 1, wherein the exit port has a radiused edge.

6. The optical fiber cap of claim 1, wherein the proximal end of the outer cap member, and a proximal end of the inner cap member, are both proximal to the reflective surface.

7. An optical fiber cap, comprising:
    a first cap member including a proximal end, a distal end, a tissue contacting surface extending therebetween, and an exit port extending through the tissue contacting surface and positioned proximal to the distal end;
    a second cap member including a proximal end and a distal end, the second cap member being attached to the first cap member distally of the exit port so as to define an interior cavity sized to receive a distal portion of an optical fiber along a first axis;
    a reflective surface angled to direct laser energy from the optical fiber along the first axis, through a firing point on the second cap member, and out of the exit port along a second axis transverse with the first axis; and
    a space formed between the first and second cap members, wherein the exit port and the space are configured to limit heat transfer between the firing point and the tissue contacting surface.

8. The optical fiber cap of claim 7, wherein the space defines a fluid flow channel configured to direct a fluid out of the exit port.

9. The optical fiber cap of claim 7, wherein, in response to laser energy, the laser firing point assumes a first temperature, the exterior tissue contacting surface assumes a second temperature, and the first temperature is a greater than the first temperature.

10. The optical fiber cap of claim 7, wherein the interior cavity extends along the first axis.

11. The optical fiber cap of claim 10, wherein the interior cavity has a constant inner diameter extending along the longitudinal axis from a proximal end of the optical fiber cap to a distal position adjacent the exit port.

12. The optical fiber cap of claim 10, wherein a proximal face of the optical fiber cap includes a first opening defined by a proximal end of the interior cavity, and a second opening defined by a proximal end of the space.

13. The optical fiber cap of claim 10, wherein a distal face of the optical fiber cap includes at least one distal facing opening in communication with a distal end of the space.

14. The optical fiber cap of claim 7, wherein the distal ends of the first cap member and the second cap member are both distal to the reflective surface, and the proximal end of the first cap member is proximal to the reflective surface.

15. An optical fiber cap, comprising:
    an inner cap nested in an outer cap;
    a tissue contacting surface on the outer cap;
    an exit port extending through the tissue contacting surface;

a cavity with an interior surface configured to receive a distal portion of an optical fiber;

a laser firing point on the interior surface of the cavity; and a reflective surface positioned in the cavity to direct laser energy discharged from the optical fiber along a first axis, through the laser firing point, and out of the exit port along a second axis transverse with the first axis, wherein distal ends of the inner cap and the outer cap are both distal to the reflective surface, wherein the tissue contacting surface is spaced apart from the laser firing point in a direction parallel with the second axis, wherein the distal end of the inner cap member is attached to the distal end of the outer cap member.

16. The optical fiber cap of claim 15, wherein the tissue contacting surface is spaced apart from the laser firing point by a space.

17. The optical fiber cap of claim 16, wherein the space extends distally along the first axis from a proximal end of the optical fiber cap to a location adjacent the laser firing point.

18. The optical fiber cap of claim 16, wherein the space surrounds the laser firing point.

19. The optical fiber cap of claim 16, wherein the a proximal portion of the optical fiber cap is engageable with the distal portion of an optical fiber.

20. The optical fiber cap of claim 19, wherein the space is placed in communication with a channel in the optical fiber when the optical fiber cap is engaged with the optical fiber.

* * * * *